United States Patent [19]
Zdarsky

[11] 3,964,170
[45] June 22, 1976

[54] GAUGE FOR POSITIONING A STOP ON THE SHAFT OF A ROOT-CANAL INSTRUMENT

[76] Inventor: Eduard Zdarsky, Brautigamstr. 5, 8 Munich 71, Germany

[22] Filed: Jan. 22, 1975

[21] Appl. No.: 542,935

[30] Foreign Application Priority Data
Apr. 3, 1974 Germany............................ 2416275

[52] U.S. Cl. ............................ 33/169 B; 33/174 D; 33/185 R
[51] Int. Cl.² ..................................... G01B 5/18
[58] Field of Search .......... 33/185 R, 169 B, 169 R, 33/107 R, 178 R, 174 D, 201, 180 R

[56] References Cited
UNITED STATES PATENTS

| | | | |
|---|---|---|---|
| 363,331 | 5/1887 | Hammer............................ | 33/178 B |
| 1,027,287 | 5/1912 | Shee................................. | 33/107 R |
| 2,059,289 | 11/1936 | Svensson...................... | 33/107 R X |
| 2,650,435 | 9/1953 | Kidd................................. | 33/169 B |

*Primary Examiner*—William D. Martin, Jr.
*Attorney, Agent, or Firm*—Karl F. Ross; Herbert Dubno

[57] ABSTRACT

A gauge for positioning a stop on a root-canal instrument is formed at one end with a handle and at the opposite end with a groove passing through a seat. The shaft of a root-canal instrument is seated in the groove with a stop fitted thereover lying in the seat. The shaft is then displaced relative to the stop and the seat such that its point travels along a scale starting at the edge of the seat so that the exact distance between the point and the stop can be determined. In addition the base plate forming this gauge is provided with a plurality of sockets each releasably holding a stop and is formed with a set of throughgoing gauge holes. Thus the dentist may ascertain with these gauge holes the diameter of the shaft of his root-canal instrument and then choose an appropriately sized stop from a selection thereof carried directly on the gauge in the sockets.

5 Claims, 4 Drawing Figures

GAUGE FOR POSITIONING A STOP ON THE SHAFT OF A ROOT-CANAL INSTRUMENT

CROSS-REFERENCE TO RELATED APPLICATION

This application is related to my copending and commonly filed U.S. patent application Ser. No. 542,933 filed Jan. 22, 1975.

FIELD OF THE INVENTION

The present invention relates a gauge for positioning a stop on the shaft of a root-canal instrument. More particularly this invention concerns a device for ascertaining and changing the longitudinal position of the insertion stop on the shaft of such a root-canal instrument.

BACKGROUND OF THE INVENTION

Root-canal work often requires that a tool, such as a file, be inserted no more than a specific maximum distance inside the root of the tooth. Since it is physically impossible for the dentist to see what he is doing he must determine by other means just how far the tool has entered the root. To this end a full-scale X-ray is taken and the insertion distance is measured on the developed X-ray.

It is possible either to use a tool having a shaft extending beyond the handle by the predetermined maximum length, or more commonly, to fit an adjustable stop on the shaft. Such a stop may be a simple block of elastic material, or may be constructed of a housing and a compression spring as described in my above-cited patent application. In the latter case it is frequently necessary for the dentist to fit the stop to the tool while the patient is sitting there with his mouth held open. Thus it is mandatory that the operation be carried out with maximum speed. At the same time it is essential that stops be placed with perfect accuracy, as otherwise the possibility of poking beyond the tooth into the jawbone is presented. This fitting operation is particularly difficult when a relatively hard-to-slide stop as described in my above-cited copending application is employed. Traditionally the dentist simply pulls the stop along the shaft to what appears to be the proper location, then measures the length of shaft protruding and adjusts the position of the stop in several operations until it is correct. Obviously such a method is time-consuming, especially when following the lengthy operation of finding a stop properly sized for the tool in question.

OBJECTS OF THE INVENTION

It is therefore an object of the present invention to provide an improved arrangement for positioning a stop on the shaft of a root-canal instrument.

Another object is the provision of an improved gauge allowing the rapid positioning of the stop with no loss in accuracy.

Another object is to provide a gauge which makes it possible for the dentist to readily and accurately select the proper stop and position it precisely on the shaft of the root-canal instrument.

SUMMARY OF THE INVENTION

These objects are attained according to the present invention in a gauge comprising a base plate formed with a seat that is adapted to receive the stop on the shaft and that has an edge, and a scale on the plate starting at the edge such that when a stop on a shaft is fitted into the seat and engaged against the edge the point of the shaft will lie on the scale at a position exactly indicating how far it projects beyond the abutment face of the stop. Thus the dentist need merely fit a stop over the very end of the tool, fit the stop and shaft of the tool upon the gauge and then press the shaft through the stop until its point lies at exactly the desired distance on the scale. It is therefore possible according to the present invention to accurately position the stop on the shaft in simple and easy operation that takes only a few seconds.

According to a feature of this invention the base plate is formed also with a groove passing through the seat and adapted to receive the shaft. The scale is in line with the groove and both the groove and the seat are provided adjacent an end of the elongated base plate. Thus the shaft is fitted in the groove with the stop in the sea and the shaft is then slid in line with the groove along the base plate with its point progressing along the scale. The opposite end of the base plate is formed as a handle or grip for the user.

In accordance with another feature of this invention there are provided on the base plate holders for variously sized stops. These holders are constituted as depressions or sockets in the base plate each provided with a respective throughgoing hole so that the dentist need merely poke the end of the shaft through the appropriately sized stop held in a respective holder and then adjust its position as described above. This operation also takes very little time.

According to yet another feature of this invention the base plate is formed with a succession of differently sized gauge holes so that the dentist readily can determine the outer diameter of the tool he is using so that he is able to then choose the properly size stop.

The seat according to this invention has a pair of sides which are inclined relative to one another, tapering together away from the upper side of the plate. This insures that the stop is snugly gripped and engaged as it is positioned on the shaft.

The gauge according to the present invention can be made relatively inexpensively of a heat-resistant synthetic resin or of metal, such as aluminum. It has an extremely long service life as it has no moving parts. Furthermore it is so simple that the dentist can learn to use it with no hardship. This device allows a very rapid positioning of the stop and use of various root-canal instruments. It is particularly adapted for use with a stop as described in my above-cited copending patent application, since the principal advantage of this stop, i.e. its ability to tightly hug the shaft, makes it difficult to slide along the shaft.

BRIEF DESCRIPTION OF THE DRAWING

The above and other objects, features, and advantages of the invention will become more readily apparent from the following description, reference being made to the accompanying drawing, in which.

SPECIFIC DESCRIPTION

Figure 1:
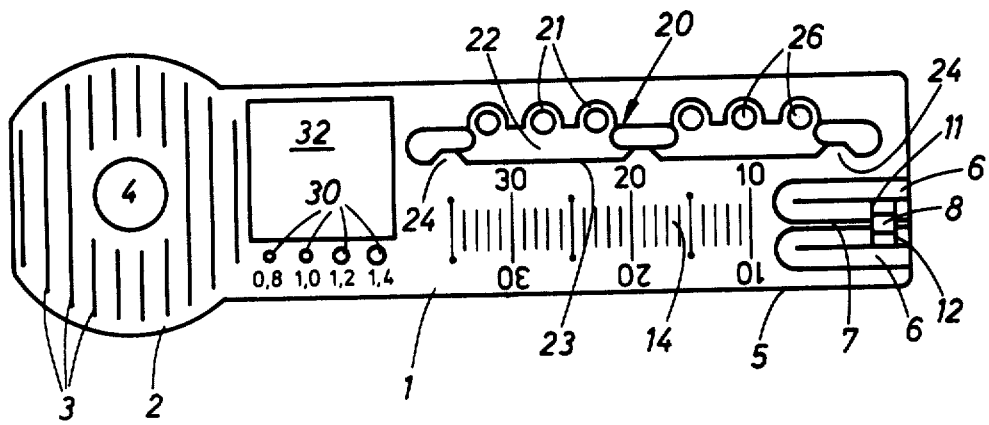
FIG. 1 is a top view of a gauge according to the present invention.
Figure 2:
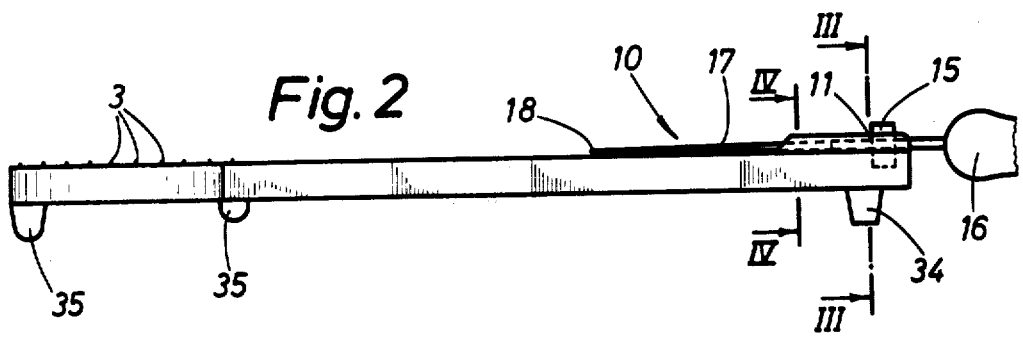
FIG. 2 is a side view of the gauge shown in FIG. 1 with a root-canal instrument in place.
Figure 3:
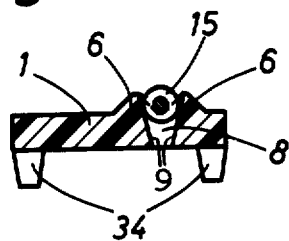
FIGS. 3 and 4 are sections taken along lines III—III and IV—IV of FIG. 2, respectively.
Figure 4:
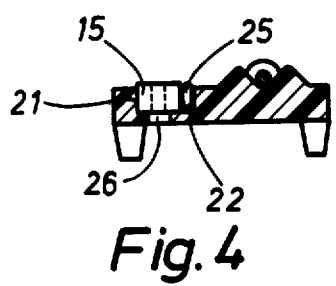

As shown in FIGS. 1 – 4 a gauge according to the present invention comprises a plate 1 made of a synthetic resin capable of withstanding heat above 250°C so as to be sterilizable. This plate 1 is formed at one end with a handle or grip 2 having transverse antislip ridges 3 and formed with a throughgoing large-diameter hole allowing the base plate 1 to be hung up. At its other end the base plate 1 is formed with a pair of parallel ridges 6 which extend parallel to the straight longitudinal edges 5 of the plate 1 and which define a longitudinally extending groove 7 terminating at the end of the plate 1 opposite the handle 2.

A seat 8 formed in the groove 7 between two inclined sides 9 generally parallel to the edges 5 has one end surface 11 toward the handle 2 and an opposite surface 12, the surfaces 11 and 12 lying transverse to the flanks of the groove 7.

In addition the plate 1 has an elongated scale 14 reading from 10 to 35 mm, with the 10-mm marking being exactly 10 mm from the edge 11 of the seat 8, i.e. the scale is aligned with the groove and has its origin at 11. A root-canal tool 10 having a handle 16 and shaft 17 placed with a stop 15 can then be fitted with the shaft 17 lying in the groove 7 and the stop 15 in the seat 8. The handle 16 is pressed so that the stop 15 presses against the end face 11 of seat 8 and the shaft is slid within the stop 15 until its point 18 lies on the marking on the scale 14 corresponding to the desired insertion. Should the point 18 be pushed too far, the handle can be pulled back, with the stop 15 confined by the edge 12.

In addition the base plate 1 is provided with a magazine 20 adapted to hold a plurality, here six, of stops 15. To this end the magazine 20 is formed with six holders or sockets 21 interconnected by a groove 22 in which a silcone tube 25 is fitted and held via bumps 24 so as to secure the six stops 15 therein. In addition under each of the sockets 21 there is provided a hole 26 of 2-mm diameter. These holes 26 allow the gauge user to poke the shaft 17 of a tool 10 not fitted with a stop 15 through one of the stops 15 held in one of the seats 21 and thereby fit it to the shaft 17. In order to ascertain the shaft diameter four gauge holes 30 are formed between the gauge 14 and the handle 2. These holes 30 are of diameters increasing from 0.8 mm to 1.5 mm so that the user can readily ascertain the outer diameter of the shaft 17 of the tool 10. Then he need merely poke it through the correspondingly sized stop 15 in the seat 21, pulling the stop 25 out of its seat 21 with the tool 10, and then positioning the stop 15 on the shaft 17 as described above.

A flat region 32 is provided on the base plate 1 for displaying instructions, a label, or the like. In addition the underside of the base plate 1 is provided with small feet 34 and a transverse ridge 35 allowing it to sit on a surface.

With the gauge according to the present invention it is possible for the dentist very readily to ascertain the diameter of the tool he is using, fit an appropriately sized stop to it, and then position the stop very accurately along the shaft. He is able to do this operation with the aid of a simple device he holds in his hand and which is approximately 3 inches long. The operation can be done with extreme ease and high speed.

I claim:

1. A gauge for setting the position of a stop member on a shaft of a root-canal instrument, said gauge comprising:
   an elongated base plate formed at one end with a longitudinally extending groove, and formed at the opposite end with a handle;
   a seat recessed in the flanks of said groove and defined between a pair of walls transverse to the axis of said groove whereby said walls can abut against respective end faces of said stop member when the latter is positioned in said seat, one of said walls being disposed further inwardly from said end than the other of said walls; and
   an elongated scale formed on said plate in line with said groove and provided with distance-measuring indicia having a scale origin at said one of said walls whereby the insertion of said tool into said groove with said stop member in said seat and in abutment with said one of said walls will display on said scale the precise distance from said stop member to a free end of said tool overlying said scale.

2. The gauge defined in claim 1 wherein said groove is defined between a pair of parallel ridges aligned with said scale, said plate being formed with a plurality of sockets and releasably holding said stop members, said plate being further formed with throughgoing hole below each socket and with resilient means for retaining said stop members of said plate.

3. The gauge defined in claim 1 wherein said plate is formed with a plurality of measuring holes of stepped diameter.

4. The gauge defined in claim 1 wherein said plate is composed of sterilizable material.

5. The gauge defined in claim 4 wherein said sterilizable material is a synthetic-resin with a softening point of at least 250°C.

* * * * *